United States Patent
Baumgartner et al.

(10) Patent No.: US 9,804,085 B2
(45) Date of Patent: Oct. 31, 2017

(54) DEVICE AND METHOD FOR MEASURING THE MOISTURE IN DIE CASTING MOLDS

(71) Applicant: Fondarex S.A., St-Legier (CH)

(72) Inventors: Konrad Baumgartner, Muenster (CH); Yves Gerard Laurent Huguenin-Vuillemin, St-Legier (CH)

(73) Assignee: Fondarex S.A., St-Legier (CH)

( * ) Notice: Subject to any disclaimer, the term of this patent is extended or adjusted under 35 U.S.C. 154(b) by 304 days.

(21) Appl. No.: 14/670,958

(22) Filed: Mar. 27, 2015

(65) Prior Publication Data
US 2015/0293015 A1    Oct. 15, 2015

(30) Foreign Application Priority Data

Apr. 14, 2014 (CH) ........................................ 615/14

(51) Int. Cl.

| | | |
|---|---|---|
| *B22D 2/00* | (2006.01) | |
| *B22D 17/14* | (2006.01) | |
| *B22D 17/20* | (2006.01) | |
| *B22D 17/32* | (2006.01) | |
| *G01N 21/3554* | (2014.01) | |
| *G01N 21/3504* | (2014.01) | |
| *G01N 21/85* | (2006.01) | |
| *B22C 9/06* | (2006.01) | |
| *G01N 21/15* | (2006.01) | |

(Continued)

(52) U.S. Cl.
CPC ......... *G01N 21/3554* (2013.01); *B22C 9/067* (2013.01); *B22D 17/145* (2013.01); *B22D 17/2007* (2013.01); *B22D 17/32* (2013.01); *B29C 45/34* (2013.01); *G01N 21/15* (2013.01); *G01N 21/3504* (2013.01); *G01N 21/85* (2013.01); *B29C 45/76* (2013.01); *B29C 2945/7614* (2013.01); *B29C 2945/76254* (2013.01); *G01N 21/359* (2013.01); *G01N 2021/151* (2013.01); *G01N 2021/354* (2013.01); *G01N 2021/8416* (2013.01); *G01N 2021/8578* (2013.01); *G01N 2201/024* (2013.01); *G01N 2201/062* (2013.01); *G01N 2201/064* (2013.01); *G01N 2201/0622* (2013.01); *G01N 2201/0626* (2013.01)

(58) Field of Classification Search
CPC ........ B22C 9/067; B22D 2/00; B22D 17/145; B22D 17/2007; B22D 17/32; G01N 21/3554
USPC .................... 164/4.1, 150.1, 154.1; 73/73
See application file for complete search history.

(56) References Cited

U.S. PATENT DOCUMENTS

| | | | | |
|---|---|---|---|---|
| 4,171,918 A | * | 10/1979 | Mactaggart | .......... G01N 21/314 250/238 |
| 6,125,911 A | * | 10/2000 | Wust et al. | ............ B22D 17/32 164/113 |
| 8,236,164 B2 | * | 8/2012 | Gustafsson et al. | . G01N 27/223 204/430 |

* cited by examiner

*Primary Examiner* — Kevin P Kerns
(74) *Attorney, Agent, or Firm* — Maginot, Moore & Beck, LLP

(57) ABSTRACT

A device and a method are provided for measuring the moisture in die cast molds, the cavity of which is connected via an evacuation conduit to an evacuation device. The modular assembly of the device is connectable to the evacuation conduit and includes a sensor assembly to measure the moisture of gases evacuated from the mold cavity. The sensor assembly includes an emitter emitting electromagnetic radiation and a detector detecting electromagnetic radiation. On the basis of the measured values obtained during the evacuation action it can be determined whether (Continued)

the amount of a water/release agent mixture jetted into the mold cavity needs to be altered before the actual casting action.

17 Claims, 3 Drawing Sheets

(51) Int. Cl.
*B29C 45/34* (2006.01)
*G01N 21/359* (2014.01)
*B29C 45/76* (2006.01)
*G01N 21/84* (2006.01)

DEVICE AND METHOD FOR MEASURING THE MOISTURE IN DIE CASTING MOLDS

BACKGROUND

This application claims priority to co-pending Swiss application No. 00615/14, filed on Apr. 14, 2014.

The invention relates to a device for measuring the moisture in die casting molds as well as to a method for measuring the moisture in die casting molds.

To permit removal of the finished casting after solidification from the mold in die casting the cavity of the mold is sprayed with a release agent. Such release agents are preferably mixed with water in the ratio of 1:100 before being sprayed. When the release agent mixed with water is sprayed hot, all of the water evaporates ideally leaving just a thin film of release agent achieving release of the casting and preventing the metal sticking to the mold. In addition to functioning as a medium carrying the release agent the water can also have the further function of cooling the casting mold. One of the problems involved in using a release agent mixed with water is that, for one thing, enough water must be used to ensure a full spraying of the walls of the cavity whilst ensuring sufficient cooling of the mold. For another, the amount of water must not be so much that there is a risk of the water not being fully evaporated, resulting in inclusions of water or water vapor in the casting on completion of casting, which, of course, is unwanted and resulting in quality deficiencies in the finished casting. This is why it would be an advantage when an indication could be made as to whether the water has more or less evaporated or whether water residues remain in the mold.

One obvious variant for measuring the moisture content in die cast molds would involve arranging one or more sensors within the die cast mold by means of which the moisture content can be measured. But because the die cast mold, depending on the metal to be casted may be hot to a few hundred to more than a thousand degrees, such a solution is impracticable since hardly any sensor is able to furnish precise results in measurement under such harsh conditions over any lengthy period of time, especially since the molten metal could also damage and/or pollute the sensor.

SUMMARY

Thus the object of the present invention is to provide a device for measuring the moisture in die casting molds by means of which it is now easy to obtain a reliable indication as to the amount of water remaining in the mold after spray application of the water/release agent mixture.

In accordance with one aspect of the disclosure a device can be connected to the evacuation conduit and comprising a sensor assembly by means of which the moisture in the gases exhausted from the mold cavity is measurable, the measurement can be implemented remote from the harsh and hot environment of the die casting machine or die cast mold. Such a device can be easy and quickly installed in a new or already existing evacuation conduit.

In one embodiment it is provided for that the sensor assembly comprises at least one emitter emitting electromagnetic radiation and at least one detector for detecting electromagnetic radiation and the device is provided with a duct for conducting the exhausted gases, the duct passing through between the emitter and the detector. This configuration makes it particularly simple to add it to the device.

In another preferred further embodiment the emitter emits electromagnetic radiation in a wavelength ranging from 600 nm to 1400 nm, preferably from 900 nm to 990 nm, particularly preferred from 930 nm to 950 nm. By adapting the wavelength range to the specific requirements, namely detecting the water content in the inflow of gas, unwanted disturbance factors are practically eliminated.

Preferably the wavelength range detected by the detector is limited by providing an upstream bandpass filter, i.e. a cost-effective means for selecting a wavelength range.

In yet another preferred further embodiment the emitter comprises at least three LEDs emitting the electromagnetic radiation and the detector comprising a corresponding number of LEDs detecting the electromagnetic radiation. This enables a larger range to be detected whilst compensating any failure of an emitter LED and/or a detector LED as the case may be.

In a further preferred further embodiment of the device the LEDs of the emitter emit electromagnetic radiation with a wavelength of 940 nm+/−5 nm and the LEDs of the detector are provided with an integrated bandpass filter passing electromagnetic radiation ranging from 935 nm to 945 nm. This wavelength range has a particularly good record of success in detecting the moisture existing in the streaming through-flow of gas.

Preferably a perforated disk is provided downstream of the emitter LEDs and/or upstream of the detector LEDs. A perforated disk is a particularly simple and cost-effective means of preventing interference between the radiation—signals—emitted by the individual LEDs.

Where a plurality of LEDs is provided, these are preferably arranged distributed over the cross-section of the duct so that the moisture existing in the throughflow of gas is detected not just pointwise or stripwise.

In yet another further preferred embodiment of the device the emitter and/or the detector are arranged upstream of a glass disk which permits passage more or less of the radiation emitted by the emitter in each case. One such glass disk is effective in warding off unwanted external effects and damaging influences without, however, having a negative effect on the measurement result.

In an alternative further embodiment the glass disk is provided with a bandpass filter which passes electromagnetic radiation within a certain wavelength range. This too, is a possibility of selectively limiting the wavelength range emitted or detected.

Preferably arranged upstream of each glass disk is a cleaning nozzle provided with at least one jetting orifice arranged such that via the jetting orifice(s) a jet of a cleaning medium can be directed at each glass disk, thus making it simple to clean each glass disk.

Because the device is configured as a modular assembly it can be incorporated with no problem in any new or existing evacuation conduits.

As is particularly preferred the device features a casing provided with an input flange, an output flange and a duct guiding from the input flange through the casing to the output flange, on one side of the duct the emitter is arranged and diametrically opposed thereto the detector. Such a device is particularly simple to be included in the evacuation conduit.

In yet a further preferred further embodiment the device comprises at least one plug-in module in the casing mounting the emitter and/or the detector and/or the glass disk(s). This configuration simplifies cleaning the glass disk and makes it easy to replace the glass disk, the emitter and/or the detector.

Preferably the device is provided with an interface via which the sensor assembly is powered electrically and/or the measurement data communicated. This facilitates a speedy integration in the die cast machine or in connecting it to its controller.

A further object of the present invention involves a method for measuring the moisture in die cast molds by means of a device configured in accordance with any of the preceding claims.

This object is achieved in accordance with one aspect of the present disclosure by automatically evacuating the moisture content of the die cast mold via an evacuation conduit and measuring during evacuation the water content of the gas streaming through the evacuation conduit by means of said device the humidity in each die cast mold can be sensed during a normal casting cycle without having to lengthen the casting cycle.

Thus in one preferred further embodiment of the method in accordance with the invention during the evacuation action a measurement cycle is implemented with a plurality of individual measurements from which an average is obtained. The advantage of this is that the measurement result is not persistently falsified or influenced by irregularities such as, for example, by renegade solids particles entrained in the exhausted gases.

Preferably before every measurement cycle zero calibration of the sensor assembly is implemented so as to practically eliminate errors due to inaccuracies in measurement prompted, for example, by changes in temperature or soiled glass disks.

In a further aspect, a method is provided for determining or altering the quantity of a water/release agent mixture sprayed into the cavity of a die cast mold by means of a device configured as described above. In this method the cavity of the die cast mold is automatically evacuated via an evacuation conduit and during evacuation the water content of the gas streaming through the evacuation conduit is measured or sensed by means of the device, the absolute amount of the water/release agent mixture for subsequent spray actions is determined from the values as measured or sensed and/or a correction factor for altering the quantity of the water/release agent mixture needed to be sprayed.

DESCRIPTION OF THE FIGURES

An example variant of the device is detailed in the following with reference to the drawings in which.

DETAILED DESCRIPTION

Figure 1:
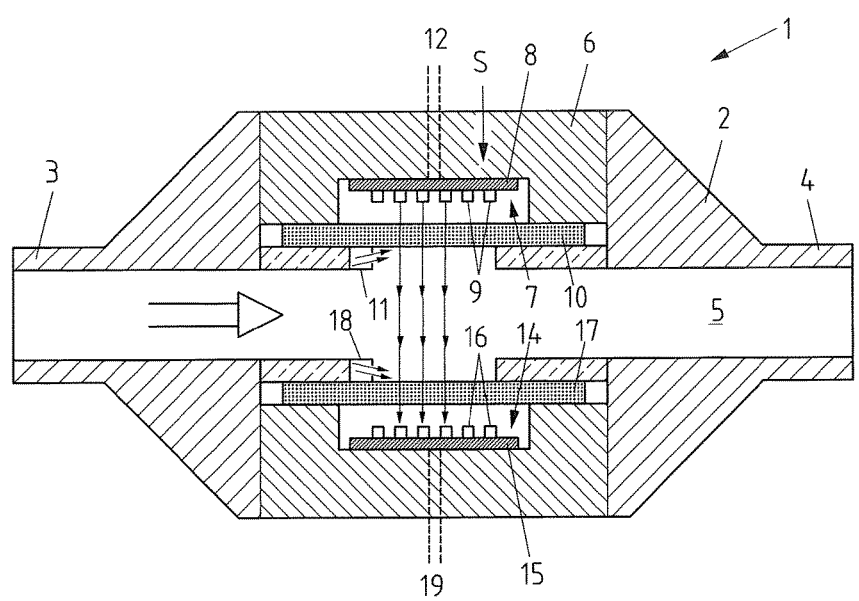
FIG. 1 is a section through a device for measuring the moisture in die cast molds depicted diagrammatically.

The configuration of the device will now be detailed with reference to FIG. 1 showing diagrammatically an example variant of a device 1 for measuring the moisture in die cast molds, the mold cavity of which is connected by an evacuation conduit to an evacuation device.

The device 1 is a modular configured component having a casing 2 provided with an input flange 3 and an output flange 4.

From the input flange 3 a duct 5 leads centrally through the casing 2 to the output flange 4. By means of the two flanges 3, 4 the device can be installed in an evacuation conduit or connected thereto. For this purpose each flange 3, 4 can be provided with a mechanical connecting means such as, for example, a male thread, a bayonet lock or the like. As an alternative a cylindrical shell surface area could also be provided to which the evacuation conduit—tube—can be attached by means of a pipe clip or adhesive band.

Housed in the casing 2 is a sensor assembly identified in all by sensor assembly S by means of which the moisture of a gas—air—streaming through the duct 5 can be determined. The sensor assembly S is mounted on a plug-in module 6 and includes an emitter 7 arranged on the one side of the duct 5 and diametrically opposed thereto a detector 14. The emitter 7 may be preferably an LED array consisting of a plurality of LEDs 9 emitting electromagnetic radiation in SMD technology on a pcb 8. An LED array with a printed circuit board "pcb" 15 and a plurality of LEDs 16 emitting electromagnetic radiation in SMD technology is also preferably made use of as the detector. Leading from each array are connecting leads 12, 19 out of the casing 2, the connecting leads 12, 19 preferably merging in a connector or an interface (both of which are not shown). Arranged upstream of each array is a glass disk 10, 17 serving as protection. Arranged upstream of each glass disk 10, 17 is a cleaning nozzle 11, 18 by means of which each glass disk 10, 17 can be cleaned by it being jetted with a cleaning agent, for instance air, as is indicated by arrows. It is understood that when speaking of LEDs 16 each sensing electromagnetic radiation in conjunction with the detector 14 this means especially photodiodes. Preferably the LEDs 9, 16 are arranged distributed over the cross-section of the duct 5.

The radiation beamed from the emitter 7 in the direction of the detector 14 must cross the duct 5 as is likewise indicated by arrows. When a medium is directed through the duct 5 this can result in the radiation arriving at the detector 14 being weakened. Since the device 1 as involved in this discussion is intended particularly to sense the water content in a streaming medium whilst minimizing the effect of possible sources of error such as, for example, foreign gases, smoke and the like, the measurement is done preferably in a specific wavelength range. Measurements in an infrared wavelength range ranging from 900 to 990 nm, particularly preferred from 930 nm to 950, especially in the range 940 nm+/−5 nm have been tested for a proven record of success. To limit the wavelength range a bandpass filter can be arranged either downstream of the emitter 7, upstream of the detector 14 or downstream of the emitter 7 and upstream of the detector 14, although, of course, emitter 7 and/or detector 14 can be put to use with integrated bandpass filters. Another variant involves providing one and/or the other glass disk 10, 17 with a bandpass filter or configured as bandpass filters.

It would also be basically possible to implement the measurement in a wavelength ranging from 600 nm to 1400 nm, a certain bandwidth then being selected within this range.

Figure 2:
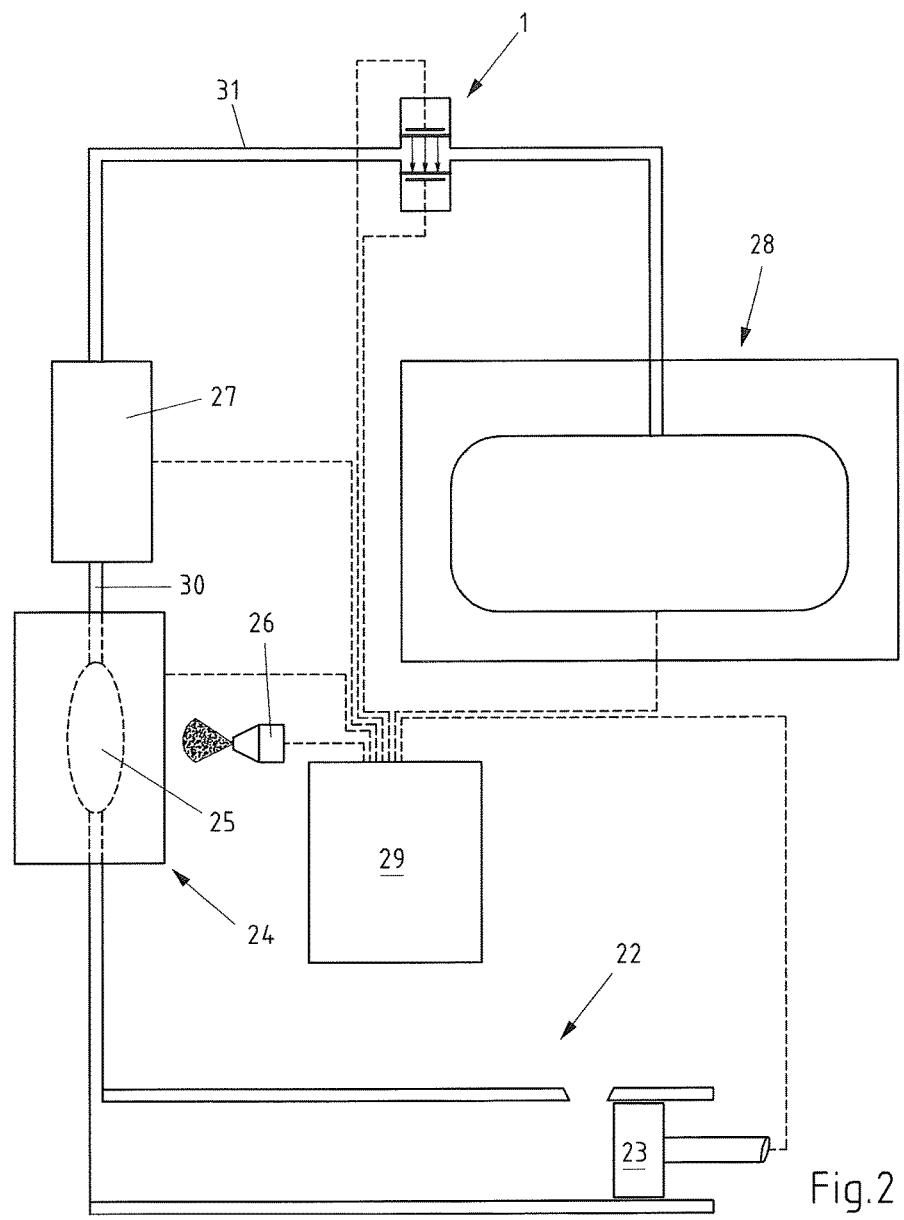
FIG. 2 is a diagrammatical representation of the device together with components of a die casting machine.

Referring now to FIG. 2 there is illustrated greatly simplified the device 1 together with a few components of a die cast machine to aid in now explaining how the moisture in die cast molds can be sensed. Indicated as components of the die cast machine are a casting chamber 22, a die casting mold 24, a sprayer head 26, an evacuation valve 27, an evacuation device 28, a controller 29 and an evacuation conduit 31.

Since the cited components 22, 24, 26, 27, 28, 29, 31 of the die cast machine are known in general they are mentioned only briefly or in conjunction with the device configured in accordance with the invention.

The casting chamber 22 is provided with a casting piston 23 by means of which the molten casting material—metal—is directed into the mold cavity 25 of the die casting mold 24. The mold cavity 25 merges at the outlet end via an evacuation duct 30 in the evacuation valve 27 which in turn is connected via the evacuation conduit 31 to the evacuation device in the form of a vacuum tank 28. The task of the evacuation valve 27 is to prevent molten casting material escaping from the mold cavity 25 into the environment or into the evacuation conduit 31. Disposed between the evacuation valve 27 and the evacuation device 28 is in the evacuation conduit 31 the device 1 for measuring the moisture in the die casting mold 24. The sprayer head 26 serves spray application of a release agent so that the completed casting can be removed from the die casting mold 24 after solidification. The release agent for application is preferably mixed with water in roughly the ratio 1:100 and jetted into the mold cavity 25 of the hot die cast mold with the die casting mold 24 open so that after evaporation of the water a thin film of release agent remains on the walls of the mold cavity 25. It is this film of release agent that enables release of the casting and preventing the metal from sticking to the mold or to the walls of the mold cavity 25. The controller 29 is electrically wired to the device 1 as well as to the components 23, 24, 26, 27, 28 as is indicated by the broken lines.

A measurement cycle for sensing the moisture in the die casting mold 24 is sequenced roughly as follows: With the die casting mold 24 open the water/release agent mixture is sprayed into the die casting mold 24 by means of the sprayer head 26. In addition to other parameters it is particularly the temperature of the die cast mold and the amount of the sprayed water/release agent mixture that decide whether all of the water has evaporated or only a portion thereof. After spray application of the mix the die casting mold 24 is closed. Before the actual moisture content begins, a so-called zero calibration of the sensor assembly S of the device 1 is carried out so that, for example, any soilage of the glass disks is not taken into account in the result of the measurement. After this, the mold cavity 25 is evacuated by means of the evacuation device 28 via the evacuation conduit 31 and the open evacuation valve 27 to evacuate gases from the mold cavity 25 and the ducts and conduits 30, 31 connected thereto. Once evacuation has begun then the actual measurement cycle is started by either measurements being made continually or by a plurality of single measurements being implemented. Measured is how great the attenuation of the emitted signal is or how strongly the signal detected by the detector is. Based on the attenuation or level of the signal as detected an indication as to the percentage of water particles and/or vapor in the stream of gas (air) can be estimated. To minimize the influence of possible sources of error such as foreign gases, smoke and the like measurement is particularly preferred in the aforementioned infrared wavelength range ranging from 930 to 950 nm (nanometers).

Preferably a measurement cycle consists of a plurality of discrete measurements. On the basis of the results as well as the profile indications as to the moisture in the casting mold can be obtained. However, a measurement cycle may also involve a plurality of discrete measurements, for example, as many as a 1000 such discrete measurements, from a certain number of discrete measurements, for example 10 discrete measurements, the average being sensed in taking this into account as the measured variable so that ultimately 100 measurement points would come into consideration. This enables, for example, the influence of individual or larger solid particles entrained in the gas streaming through the device to be minimized.

Depending on the results obtained from measurement the quantity of water/release agent mixture to be applied by spraying can be altered, for instance, if the water percentage is too high the quantity of the water/release agent mixture to be applied by spraying is reduced which could also involve lengthening the evacuation action.

It is usually the case that at the start of a casting cycle in which, for example, a few thousand parts are to be cast, a measurement cycle is implemented before each casting action and, if need be, the quantity of the water/release agent mixture to be applied by spraying altered, indeed so long, until the decisive parameters such as especially the temperature of the mold and the moisture of the mold cavity have settled down to a prescribed degree, it, of course, thereby being necessary to ensure that after evaporation of the water a uniform film of release agent remains throughout. After this, a measurement cycle can be implemented in predefined intervals, for example every hour or after each tenth casting action and altered depending on the values or parameters as measured or sensed, it also, of course, being possible to alter the quantity of the mix to be applied locally within the casting mold or its cavity. Again, depending on the results of the measurement changes may be undertaken to the mold itself, by, for example, providing a drilled hole at the end of a branch in the mold cavity or downstream of a plunger to evacuate the water.

The end of the evacuation action is usually also the start of the actual casting action in which after evacuation of the mold cavity the molten metal is transported by means of the casting piston into the mold cavity. But, should it be discovered during a measurement cycle that the water percentage is too high, i.e. above a predefined maximum permissible value, an alarm, for instance, can be triggered and/or the casting action halted.

From the profile of the measurement results an indication may also be obtained as to in which part or in which portions of the mold cavity water has collected at the most. If, for instance, the water content rises at the end of the evacuation action, then this is an indication that too much water exists in the smaller or narrower or lengthy "branches" of the mold cavity. Being aware of this can be made use of, where necessary, to adapt the amount of the water/release agent mixture to be sprayed only in spots or in certain regions Preferably before each measurement the two glass disks are cleaned by means of the cleaning nozzles or by a cleaning medium jetted therefrom. Should it be discovered in zero calibration preferably implemented before each measurement cycle that the glass disks are soiled strongly to excessively, a signal can be generated for example via the controller to trigger an additional cleaning of the glass disks or a replacement thereof. This is why it is of an advantage when the device 1 is configured so that the glass disks are easily accessible.

Figure 3:
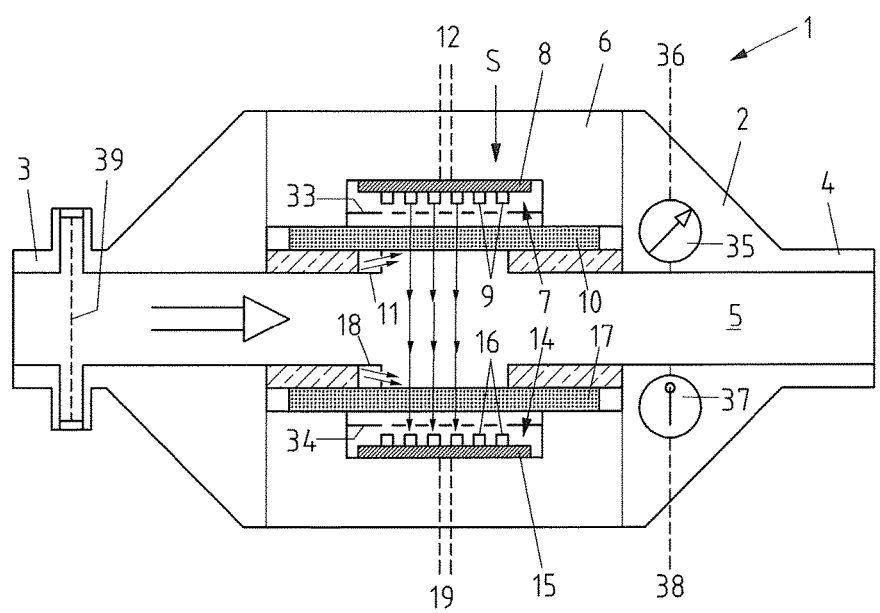
FIG. 3 is a section through an alternative configuration of a device for measuring the moisture in die cast molds, again depicted diagrammatically.

Referring now to FIG. 3 there is illustrated a section through an alternative embodiment of the device for measuring the moisture in die casting molds, only the differences as compared to the embodiment as shown in FIG. 1 being detailed, wherein like parts are identified by like reference numerals. The device 1 is provided at its inlet end with a replaceable filter 39 intended to retain particularly large solid particles in the gas streaming through the device. The filter 39 is preferably arranged replaceable in the device 1. Disposed in addition between the emitter 7 and the glass disk 10 is a perforated disk 33. The perforated disk 33 is configured such that the light emitted by the LEDs 9 of the emitter 7 is able to attain via openings—perforations—in the direction of each LED 16 assigned thereto. The size of the openings is adapted to the requirements such that any stray light, i.e. light not emitted by a certain angle is prevented from attaining the perforated disk 33. Arranged upstream of the detector 14 is a further perforated disk 34, the openings of which do not allow light impinging the perforated disk 34 outside of a predefined surface area—opening—in the direction of the detector 14. If needs be, it may be sufficient to provide just one of the two perforated disks 33 or 34, but in any case any interference is to be avoided by the perforated disk(s). In this example use may also be made of LEDs 9 which emit light in a narrow wavelength range, preferably in the range 940+/−5 nanometers. Preferably LEDs 16 having an integrated bandpass filter are put to use which likewise allow only light in the predefined wavelength range to pass.

Tests have shown that preferably between two and eight emitter LEDs 9 and a corresponding number of detector LEDs 16 best find application, particularly preferred being between three and six emitter LEDs 9 and a corresponding number of detector LEDs 16. Providing at least three emitter and detector LEDs permits compensation should an emitter and detector LED become defective, it being obvious that the more LEDs employed the less the sensitivity as regards failure of any one LED. Likewise, the more the number of LEDs the less the sensitivity as regards a partial soilage of the glass disk(s). Making use of four or five emitter and detector LEDs has a proven record of success as regards sensitivity, reliability, space availability and the costs. Preferably the LEDs are not arranged—as shown in the drawing—parallel to the longitudinal centerline but in a row at right angles to the longitudinal centerline of the device 1 so that substantially the full cross-section of the duct 5 is detected.

Provided in addition, is a pressure sensor 35 by means of which the pressure prevailing in the duct 5 can be sensed. Via a connecting lead 36 the pressure sensor 35 can be connected to the controller 29 (FIG. 2). Also provided is a temperature sensor 37 by means of which the temperature of the gas streaming through the device can be sensed. Via a connecting lead 38 the temperature sensor 37 can be connected to the controller 29 (FIG. 2). By providing a pressure sensor 35 it is possible to sense not only the pressure prevailing in the duct 5 but it can also be additionally determined whether a stream of gas in the duct 5 exists. If necessary, for this purpose a comparison can be made with a further pressure sensor (not shown). Since it is usually the case that a further pressure sensor is arranged in the die cast mold recourse can be made to its data, for example. The cited sensors 35, 37 are also especially suitable for comparing the various measurements to each other and, where necessary, by means of a controller influencing the amount of the water/release agent mixture jetted into the die cast mold. But in any case, if required, only the pressure sensor 35 or temperature sensor 37 may be provided, although, of course, more than just one pressure sensor and/or more than just one temperature sensor may be provided.

It is understood that the example embodiments of the device as explained above are not to be considered as being conclusive, but that in the scope of the protection as afforded by the claims other configurations are definitely possible. Thus, for instance, two plug-in modules could be provided, one part accommodating the emitters inclusive the corresponding glass disk whilst the other part accommodates the detectors inclusive the corresponding glass disk. Such a configuration makes it particularly simple to clean or replace each glass disk, emitter or detector. And, of course, two emitters and two detectors could be provided, for example, arranged in line along the duct 5 or each at right angles to each other along the circumference of the duct 5.

The salient advantages afforded by the device as shown can be summarized as follows:

The device now makes it possible to reliably measure/sense any residual amount of water in the casting mold;

By the device being sited remote from the casting mold and thus from the hot zone of the die cast machine its thermal load is comparatively slight;

The device is configured simple and cost-effective;

The device can be easily and quickly integrated in existing or new systems;

The device has no influence on the casting cycle.

LIST OF REFERENCE NUMERALS 1. device
2. casing
3. input flange
4. output flange
5. duct
6. module
7. emitter
8. pcb
9. LEDs
10. glass disk
11. cleaning nozzle
12. connections
14. detector
15. pcb
16. LEDs
17. glass disk
18. cleaning nozzle
19. connections
22. molding chamber
23. casting piston
24. die casting mold
25. mold cavity
26. spray head
27. evacuation valve
28. vacuum tank
29. controller
30. evacuation duct
31. evacuation conduit
33. perforated disk
34. perforated disk
35. pressure sensor
36. connecting lead
37. temperature sensor
38. connecting lead
39. filter

What is claimed is:

1. A device for measuring the moisture in die cast molds, a cavity of which is connected via an evacuation conduit to an evacuation device, characterized in that said device is connectable to the evacuation conduit and comprises a sensor assembly by means of which moisture in gases exhausted from the cavity is measured, wherein said sensor assembly includes at least three LED emitters emitting electromagnetic radiation and a corresponding at least three detectors for detecting electromagnetic radiation;

the device is provided with a duct for conducting the exhausted gases, the duct passing through between the at least three LED emitters and the at least three detectors; and said duct defines a cross-section and said at least three LED emitters and said at least three detectors are arranged distributed over the longitudinal cross-section of the duct.

2. The device as set forth in claim 1, characterized in that each of said at least three LED emitters emits electromagnetic radiation in a wavelength ranging from 600 nm to 1400 nm.

3. The device as set forth in claim 2, characterized in that provided upstream of the at least three detectors is a bandpass filter which passes electromagnetic radiation within a wavelength range ranging from 900 nm to 990 nm.

4. The device as set forth in claim 2, characterized in that each of said at least three LED emitters emits electromagnetic radiation in a wavelength ranging from 900 nm to 990 nm.

5. The device as set forth in claim 4, characterized in that each of said at least three LED emitters emits electromagnetic radiation in a wavelength ranging from 930 nm to 950 nm.

6. The device as set forth in claim 1, characterized in that each of said at least three LED emitters emits electromagnetic radiation with a wavelength of 940 nm+/−5 nm and the at least three detectors are provided with an integrated bandpass filter passing electromagnetic radiation ranging from 935 nm to 945 nm.

7. The device as set forth in claim 1, characterized in that to prevent interferences a perforated disk is provided downstream of the at least three LED emitters and/or upstream of the at least three detectors.

8. The device as set forth in claim 1, characterized in that said at least three LED emitters are arranged upstream of a glass disk which permits passage of the radiation emitted by each of the at least three emitters.

9. The device as set forth in claim 8, characterized in that said glass disk is provided with a bandpass filter which passes electromagnetic radiation within a certain wavelength range ranging from 900 nm to 990 nm.

10. The device as set forth in claim 9, characterized in that said glass disk is provided with a bandpass filter which passes electromagnetic radiation within a wavelength range from 930 nm to 950 nm.

11. The device as set forth in claim 8, characterized in that arranged upstream of said glass disk is a cleaning nozzle provided with at least one jetting orifice arranged such that via the jetting orifice(s) a jet of cleaning medium is directed at said glass disk.

12. The device as set forth in claim 1, characterized in that said at least three detectors are arranged upstream of a glass disk which permits passage of the electromagnetic radiation at least in a certain wavelength range.

13. The device as set forth in claim 1, characterized in that said device is configured as a modular assembly.

14. The device as set forth in claim 13, characterized in that said device comprises a casing provided with an input flange, an output flange and a duct guiding from the input flange through the casing to the output flange, wherein on one side of the duct the at least three LED emitters are arranged and diametrically opposed thereto the at least three detectors.

15. The device as set forth in claim 14, characterized in that each flange is configured to be connected to an evacuation conduit.

16. The device as set forth in claim 14, characterized in that said device comprises at least one plug-in module in the casing, said module mounting the at least three LED emitters and/or the at least three detectors and/or the glass disk.

17. The device as set forth in claim 1, characterized in that said sensor assembly generates sensed data corresponding to a measurement of the gases exhausted, and said device is provided with an interface via which the sensor assembly is powered electrically and/or the sensed data communicated.

* * * * *